(12) United States Patent
Jackson

(10) Patent No.: US 11,982,571 B2
(45) Date of Patent: May 14, 2024

(54) SYSTEMS AND METHODS FOR STUDYING ROTATIONAL HEAD INJURY

(71) Applicant: University of South Florida, Tampa, FL (US)

(72) Inventor: Travis Corey Jackson, Tampa, FL (US)

(73) Assignee: University of South Florida, Tampa, FL (US)

( * ) Notice: Subject to any disclaimer, the term of this patent is extended or adjusted under 35 U.S.C. 154(b) by 96 days.

(21) Appl. No.: 17/734,568

(22) Filed: May 2, 2022

(65) Prior Publication Data

US 2022/0357209 A1 Nov. 10, 2022

Related U.S. Application Data

(60) Provisional application No. 63/183,329, filed on May 3, 2021.

(51) Int. Cl.
*G01K 1/14* (2021.01)
*G01P 3/00* (2006.01)
*G01P 15/00* (2006.01)

(52) U.S. Cl.
CPC ............... *G01K 1/14* (2013.01); *G01P 3/00* (2013.01); *G01P 15/00* (2013.01)

(58) Field of Classification Search
CPC ... G01K 1/14; G01P 3/00; G01P 15/00; G01P 15/165; A61B 5/4064; A61B 5/01; A61B 2503/40; A61B 2503/42
See application file for complete search history.

(56) References Cited

U.S. PATENT DOCUMENTS

2015/0164721 A1* 6/2015 Miyashita ............ G06V 40/161 5/617
2023/0011717 A1* 1/2023 Larson .................. A61B 5/1113

OTHER PUBLICATIONS

Barlow et al., "Late neurologic and cognitive sequelae of inflicted traumatic brain injury in infancy," Pediatrics, Aug. 2005, 116(2):e174-e185.
Bhardwaj et al., "A systematic review of the diagnostic accuracy of ocular signs in pediatric abusive head trauma, " Ophthalmology, May 1, 2010, 117(5):983-992.
Binenbaum et al., "The natural history of retinal hemorrhage in pediatric head trauma," Journal of American Association for Pediatric Ophthalmology and Strabismus, Apr. 1, 2016, 20(2):131-135.
Cheshire et al., "A systematic autopsy survey of human infant bridging veins," International Journal of Legal Medicine, Mar. 2018, 132(2): 13 pages.
Chevignard et al., "Long-term outcome of abusive head trauma," Pediatric radiology, Dec. 2014, 44(4):S548-S558.
Christian et al., "The Eye Examination in the Evaluation of Child Abuse," Pediatrics, 2018, 142(2): 10 pages.

(Continued)

*Primary Examiner* — Xin Y Zhong
(74) *Attorney, Agent, or Firm* — Owen G. Behrens; Smith & Hopen, P.A.

(57) ABSTRACT

The disclosure provides a cranial rotation system, including a subject stage configured to support a subject; a cranial support configured to support a cranium of the subject and rotate relative to the subject stage; subject stage a motor configured to rotate the cranial support about a rotational axis; and a controller configured to operate the motor.

20 Claims, 11 Drawing Sheets

(56) References Cited

OTHER PUBLICATIONS

Eppig et al., "The International Mouse Strain Resource (IMSR): cataloging worldwide mouse and ES cell line resources," Mammalian Genome, Oct. 2015, 26(9):448-455.
Finnie et al., "Neuropathological changes in a lamb model of non-accidental head injury (the shaken baby syndrome)," Journal of clinical neuroscience, Aug. 1, 2012, 19(8): 7 pages.
Goldstein et al., "Abnormal neuroimaging is associated with early in-hospital seizures in pediatric abusive head trauma," Neurocritical care, Aug. 2011, 15(1):63-69.
Hanlon et al., "Minocycline transiently reduces microglia/macrophage activation but exacerbates cognitive deficits following repetitive traumatic brain injury in the neonatal rat," Journal of Neuropathology & Experimental Neurology, Mar. 1, 2016, 75(3):214-226.
Kabadi et al., "Fluid-percussion-induced traumatic brain injury model in rats," Nature protocols, Sep. 2010, 5(9):1552-1563.
Kalish et al., "Weight drop models in traumatic brain injury," InInjury models of the central nervous system, Humana Press, 2016, 193-209.
Kochanek et al., "Pre-clinical models in pediatric traumatic brain injury—challenges and lessons learned," Child's Nervous System, Oct. 2017, 33(10):1693-1701.
Matschke et al., "Erratum to: Encephalopathy and death in infants with abusive head trauma is due to hypoxic-ischemic injury following local brain trauma to vital brainstem centers," Int J Legal Med, 2015, 129:115-116.
Matschke et al., "Nonaccidental head injury is the most common cause of subdural bleeding in infants< 1 year of age," Pediatrics, Dec. 2009, 124(6):1587-1594.
Narang et al., "Abusive head trauma in infants and children," Pediatrics, Apr. 1, 2020, 145(4): 7 pages.
Orman et al., "MRI findings in pediatric abusive head trauma: a review," Journal of Neuroimaging, Jan. 2020, 30(1):15-27.
Osier et al., "The controlled cortical impact model: applications, considerations for researchers, and future directions, " Frontiers in neurology, Aug. 17, 2016, 7(134): 14 pages.
Rowe et al., "Midline (central) fluid percussion model of traumatic brain injury in pediatric and adolescent rats," Journal of Neurosurgery: Pediatrics, Jul. 1, 2018, 22(1):22-30.
Rumalla et al. "Nationwide incidence and risk factors for post-traumatic seizures in children with traumatic brain injury," Journal of Neurosurgery: Pediatrics. Sep. 21, 2018;22(6):684-693.
Sidpra et al., "Rise in the incidence of abusive head trauma during the COVID-19 pandemic," Arch Dis Child, Mar. 2021, 106(3): 1 pages.
Starling et al., "Analysis of perpetrator admissions to inflicted traumatic brain injury in children," Archives of pediatrics & adolescent medicine, May 1, 2004, 158(5):454-458.
Tung et al., "Comparison of accidental and nonaccidental traumatic head injury in children on noncontrast computed tomography," Pediatrics, Aug. 2006, 118(2):626-633.
Vester et al., "Modeling of inflicted head injury by shaking trauma in children: what can we learn?" Forensic Science, Medicine and Pathology, Sep. 2019, 15(3): 15 pages.
Wang et al., "Pathophysiological and behavioral deficits in developing mice following rotational acceleration-deceleration traumatic brain injury," Disease models & mechanisms, Jan. 1, 2018, 11(1): 10 pages.
Williams et al., "Penetrating ballistic-like brain injury in the rat: differential time courses of hemorrhage, cell death, inflammation, and remote degeneration," Journal of neurotrauma, Dec. 1, 2006, 23(12):1828-1846.
Wittschieber et al., "Understanding subdural collections in pediatric abusive head trauma," American Journal of Neuroradiology, Mar. 1, 2019, 40(3):388-395.
Joyce et al., "Pediatric Abusive Head Trauma," StatPearls Publishing, 2020, 24 pages.

* cited by examiner

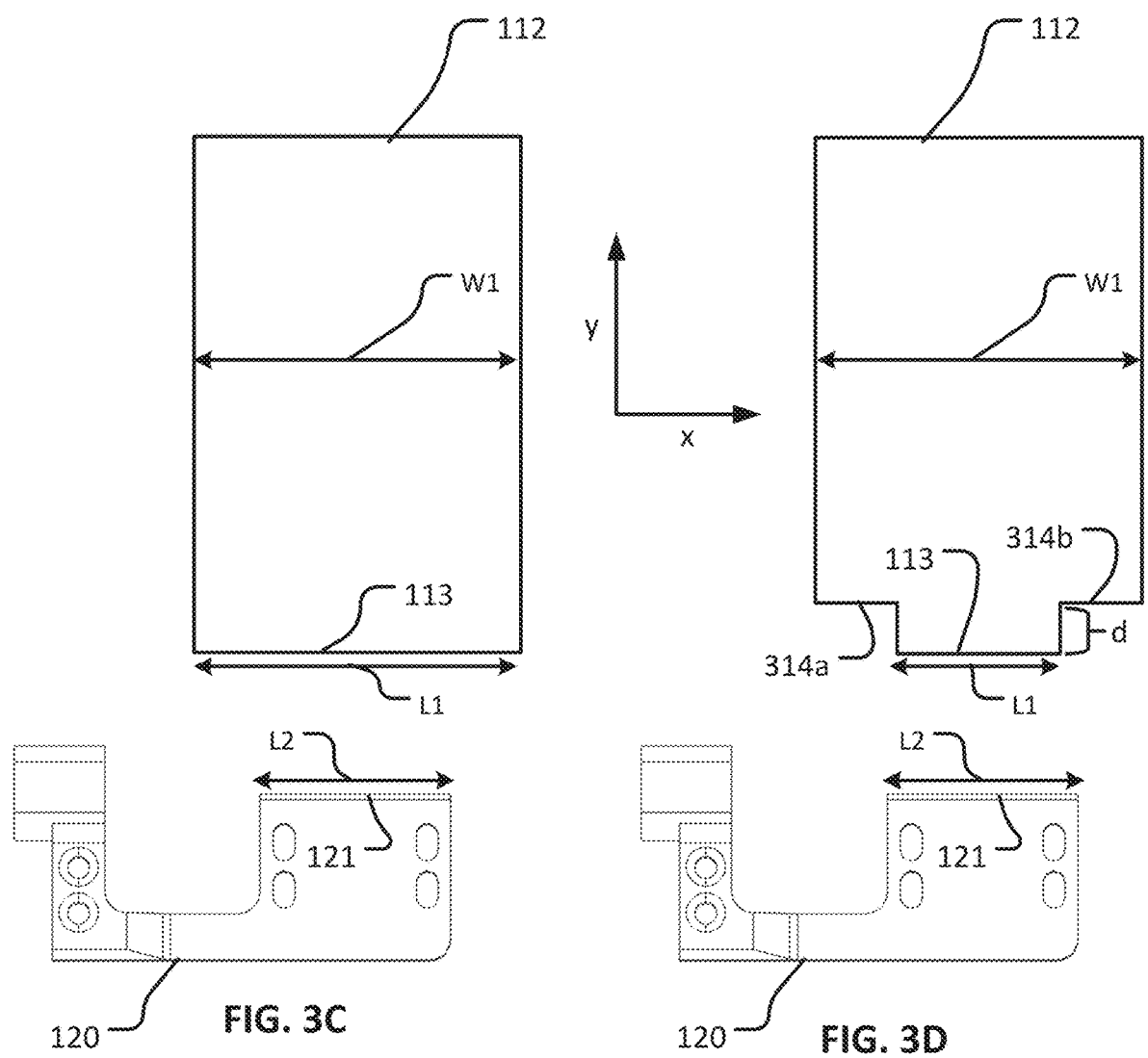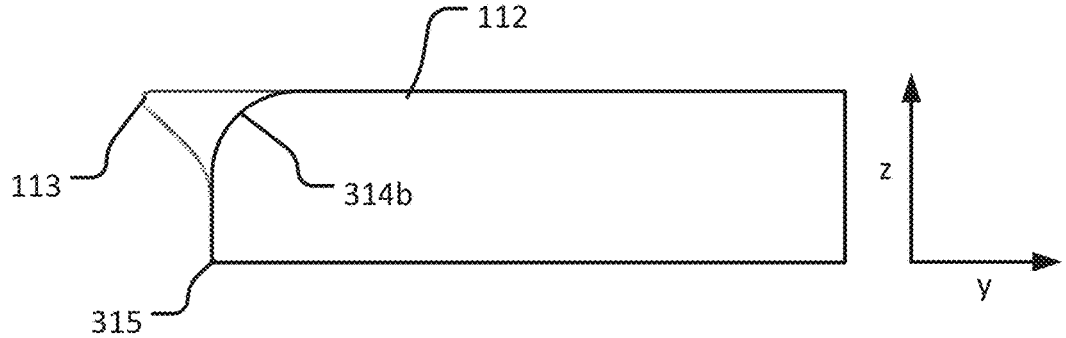

SYSTEMS AND METHODS FOR STUDYING ROTATIONAL HEAD INJURY

FIELD OF THE DISCLOSURE

The disclosure relates to systems and methods for studies on brain damage.

BACKGROUND

Abusive head trauma (AHT) is a leading cause of death and disability from child abuse. Shaken Baby Syndrome (SBS) is a subset of AHT stemming from an infant's weak neck muscles predisposing the head to rotational acceleration-deceleration shearing forces. Greater understanding of AHT relies upon the use of animal and experimental mechanical models. Rat and murine models can imitate AHT in the infant, partially duplicating the pathology observed in severe AHT seen clinically, including the presence of subdural and subarachnoid hemorrhage, brain swelling, and retinal hemorrhage. There is a need of devices and methods that simulate rotational acceleration-deceleration injury forces frequently attributed to brain damage in infants.

Current models of rodent AHT utilize a gas-driven piston to accelerate a metal projectile which strikes a receiver connected to a head-plate and produces the head acceleration in a single direction. Injuring only one side of the brain is not clinically relevant in the setting of shaking injuries, and the use of a gas-driven system requires a large laboratory footprint (i.e., to install a large gas tank).

SUMMARY

The present disclosure relates to techniques that produce forces to simulate rotational acceleration-deceleration injury that may result in damages in children such as abusive head trauma (AHT) or other types of brain damages. In some embodiments, such techniques can be used to study shaken-baby syndrome (SBS) in pre-clinical rodent research, using for example neonatal rats or mice. The devices and methods according to embodiments of the present disclosure permit rigorous and robust studies on brain damages in rodents that are induced by rotational acceleration/deceleration injury.

Disclosed herein is a rodent cranial acceleration system including a motor connected with a cranial support, a subject stage, and a controller in electronic communication with the motor. A subject, such as a rodent subject, is arranged upon a subject stage and the head of the subject affixed to the cranial support. The subject stage is positioned with respect to the cranial support. In some embodiments, the spine of the subject can be aligned substantially with the sagittal plane. Further, a rotational axis of the cranial support can be transverse (e.g., perpendicular) to a cervical vertebra of the subject.

In some embodiments, the motor is controlled to oscillate the cranial support to induce rotational accelerations in a head of a subject along the sagittal plane. The repetitive accelerations can induce rotational acceleration-deceleration shearing forces and injury in the subject brain similar to abusive head trauma seen in infant patients. In some embodiments, the cranial support can be rotated within an angle range that can achieve desired effects to the subject head. In addition or alternatively, the cranial support can be rotated at a frequency that can achieve desired effects on the subject head. The angle range and/or the frequency can be preset by a user or preprogramed for one or more experimental scenarios.

In some embodiments, the subject stage includes a temperature control system configured to maintain targeted body temperature and hemodynamics in anesthetized subjects. For example, during injury tests, rodent subjects are prone and in contact with the subject stage for extending time periods. During such prolonged periods of injury tests, general anesthesia may depress blood circulation and body temperature in the rodent subjects which are sensitive to fluctuations in core temperatures. The temperature control system can restrict such decreasing blood circulation and body temperature, thereby allowing the injury test in an extended period of time. Some embodiments of the temperature control system can include a heating element configured to generate heat on the subject stage. Further, some embodiments of the temperature control system can include a temperature sensor. The temperature sensor can be arranged at various locations to detect, for example, a temperature of the heating element and/or a temperature at the subject stage. The detected temperature can be used to control the heating element at a predetermined temperature setting. Alternatively or in addition, the temperature sensor can include a sensor that can measure a body temperature of the subject on the subject stage.

In some embodiments, the subject stage can include a thermally conductive material that can be warmed by the heating element. The temperature sensor can be disposed to measure the temperature of the subject stage. The controller is in electronic communication with the heating element and the temperature sensor. The controller can receive a signal from the temperature sensor and use the signal to monitor and control the subject stage temperature in a way that maintains the rodent core temperature during injury tests.

The devices, system, and techniques described herein may provide one or more of the following advantages. First, some embodiments described herein provide devices and techniques that produce rotational acceleration-deceleration injury forces for SBS study in pre-clinical rodent research, thereby improving the quality of evidence that informs evidence-based guidelines across the spectrum of AHT or other types of pediatric traumatic brain injury (TBI). Further, the devices and techniques permit studies for clarifying whether standard-of-care approaches used in the clinical management of adult TBI have utility in the pediatric setting. It has been known that AHT is one of the leading causes of death or disability from abuse in children younger than 5 years old. The devices and techniques described herein can provide reliable and robust mouse AHT models and tools for researchers and clinician-scientists.

Second, the techniques described herein can use an acceleration profile of the cranial support that is controlled to allow highly repeatable injury to be provoked in the subject. For example, the cranial support can be accurately accelerated and decelerated within an angular acceleration resolution range from 500 radians/s$^2$ to 75,000 radians/s$^2$. Providing highly accurate angular accelerations to the subject cranium increases repeatability and allows consistent results to be collected across a broad range of injury test conditions.

Third, a high-torque motor generating head accelerations in both the flexion and extension directions facilitates independent control the of the injury severity to the dorsal and ventral sides of the brain, respectively. This capability allows the user to accurately model clinically-relevant abuse scenarios in rodents, in which a human perpetrator shaking the head of an infant produces rotational injuries on multiple sides of the brain.

Fourth, the techniques described herein employs a motor that is capable of providing a high level of acceleration to the cranial support allowing extreme injuries to be investigated in a controlled environment. Further, the motor can be configured to provide tightly controlled acceleration forces and thus provides increased data reliability.

Fifth, the techniques described herein can use multiple motion sensors that monitor rotational velocity and acceleration of the cranial support. For example, the acceleration of the cranial support can be monitored by two acceleration sensors configured to monitor two axes of acceleration. For example, one monitors rotational velocity, which can be used to calculate rotational acceleration. The other monitors linear/tangential acceleration. As the radius from the axis of rotation to the linear accelerometer remains fixed and the value a constant, linear/tangential acceleration can be converted mathematically into rotational acceleration. The fidelity of the acceleration of the cranial support is confirmed by calculating a correlation between the two sensor inputs germane to rotational acceleration. Determining the acceleration based on two sensor inputs measuring two independent axes can increase the reliability of the acceleration estimate provided to the controller.

The data obtained from dual motion sensors and the correlation coefficient provide users a new type of "common data element" (CDE) that has not been implemented previously into rodent models of AHT, and which will facilitate meaningful comparisons on the results of studies performed across distance and time. The National Institutes of Health supports the development of CDEs for pre-clinical and clinical TBI research. The goal of CDEs is to encourage the recording and reporting of quantifiable elements within an experiment (study parameters) which aid the interpretation of findings to account for heterogeneity in findings between studies and across research institutions. For instance, units that define the insult severity of a brain injury is a critical CDE. In the current specification, the peak rotational acceleration/deceleration establishes the insult severity. Thus, the motion sensors and motor provide data on velocity waveforms, acceleration waveforms, frequency, and total number of oscillations, which provide users critical CDEs for an AHT/SBS model.

Sixth, the techniques described herein can allow the subject stage to be positionable along three axes to a high degree of accuracy (e.g., >0.1 mm resolution). Each subject subjected to an injury test has different physical dimensions and physiologies. Precise subject stage positioning can increase injury test accuracy to a targeted vertebra.

Seventh, the devices and system described herein include an electrically powered device which uses a small footprint and is readily established in the laboratory setting. The use of electrical power provides flexibility in environment positioning and portability of the device.

In general, in a first aspect, the disclosure provides a cranial rotation system, including a subject stage configured to support a subject; a cranial support configured to support a cranium of the subject and rotate relative to the subject stage; subject stage a motor configured to rotate the cranial support about a rotational axis; and a controller configured to operate the motor.

In some embodiments, the cranial support can be disposed at an end of the subject stage. The subject stage can include a heating element in electrical connection with the controller, the controller configured to control a temperature of the heating element. The heating element can be removable from the subject stage. The subject stage can include a temperature sensor configured to detect a temperature at the subject stage and transmit a temperature signal to the controller, the temperature signal being representative of the detected temperature. The controller can be configured to operate the temperature of the heating element based at least in part upon the temperature signal. The cranial support can include an acceleration sensor configured to detect an acceleration of the cranial support and transmit an acceleration signal to the controller, the acceleration signal being representative of the detected acceleration. The acceleration sensor can include a rotational acceleration sensor, a linear acceleration sensor, or both of the rotational acceleration sensor and the linear acceleration sensor.

In some embodiments, the cranial support can include a velocity sensor configured to detect a velocity of the cranial support and transmit a velocity signal to the controller, the velocity signal being representative of the detected velocity. The velocity sensor can include a rotational velocity sensor, a linear velocity sensor, or both of the rotational velocity sensor and the linear velocity sensor. The controller can be configured to operate the motor based at least in part upon the acceleration signal. The controller can be configured to operate the motor based at least in part upon the velocity signal. The subject stage has a first end and a second end opposite to the first end, the first end being closer to the cranial support than the second end, and the first end extending along a transverse axis across a width of the subject stage, and wherein the rotational axis of the cranial support can be arranged parallel with the transverse axis. The rotational axis of the cranial support can be elevated above a top surface of the subject stage. The motor can be configured to rotate the cranial support around the rotational axis in a range from −80° to 80° with respect to an initial angle. The motor can be configured to rotate the cranial support around the rotational axis in a range from −45° to 45° with respect to an initial angle. The controller can be configured to operate the motor according to an acceleration profile. The acceleration profile can be a sinusoidal profile, a saw tooth profile, or a triangle profile.

In some embodiments, the cranial rotation system can further include a platform configured to receive the subject stage; and a platform positioner configured to alter a position of the platform. The platform positioner can include a position sensor and can be configured to detect a position of the platform positioner and transmit a position signal to the controller, the position value being representative of the position of the platform positioner along at least one spatial dimension. The controller can be configured to receive a position value from the platform positioner and control the platform positioner based on at least the position value. The subject can be a small mammalian subject. The subject can be a murine subject, or a mustelid subject.

In a second aspect, the disclosure includes a method for rotating a head of a subject using a cranial rotation device, the cranial rotation device including a subject stage, a cranial support, and a motor, and the method including positioning the subject on the subject stage; arranging the head of the subject on the cranial support; and controlling the motor to rotate the subject stage in an angle range around an axis at a frequency.

In some embodiments, the rotation of the subject stage can be in a flexion and an extension directions based on the orientation of the subject head. The subject can be a murine subject. The axis can be perpendicular to a spine of the subject. The axis intersects the spine of a subject at a cervical vertebrae. The frequency can be in a range from 1 Hz and 30 Hz. The angle range can be within ±80° of a top surface plane of the subject stage. The angle range can be within ±55° of a top surface plane of the subject stage. The angle range can be within ±45° of a top surface plane of the subject stage. The device can include a heating element and a temperature sensor, and the method can include determining a temperature value of the subject stage and controlling the heating element based on the temperature value.

In some embodiments, the method can include measuring an acceleration value of the cranial support and controller the motor based upon the acceleration value. The method can include calculating a correlation coefficient based upon at least the acceleration signal obtained by the motor encoder, direct measurement of acceleration via sensors, by the mathematical derivation of acceleration from rotational velocity data, or any combination thereof. The correlation coefficient can be a Pearson correlation coefficient. The cranial support can include a motion sensor configured to detect a motion of the cranial support and transmit a motion signal to the controller, the motion signal being representative of the detected motion. The motion sensor can be at least one of a linear velocity sensor, a rotational velocity sensor, a linear acceleration sensor, or a rotational acceleration sensor. The controller can be configured to operate the motor based at least in part upon the motion signal. The cranial support can include two or more motion sensors and the controller can be configured to receive two or more motion signals from the two or more motion sensors and calculate a correlation coefficient between the two motion signals. The two or more motion sensors are selected from a group consisting of a linear velocity sensor, a rotational velocity sensor, a linear acceleration sensor, and a rotational acceleration sensor. The controller can be configured to operate the motor based at least in part upon the two or more motion signals. The correlation coefficient can be a Pearson correlation coefficient.

The details of one or more embodiments are set forth in the accompanying drawings and the description below. Other features and advantages will be apparent from the description and drawings, and from the claims.

BRIEF DESCRIPTION OF THE DRAWINGS

FIG. 3C is a top-down view of the stage of FIG. 3A.

FIG. 3D is a top-down view of a stage having a front edge which extends a portion of the width of the stage.

FIG. 3E is a side-view of the front edge of the stage of FIG. 3D.

DETAILED DESCRIPTION

In general, the present disclosure provides a cranial acceleration system including a motor connected with a cranial support, a subject stage, and a controller in electronic communication with the motor. A subject, such as a rodent subject, is arranged upon a subject stage and the torso of the subject is temporarily affixed to the stage. The head of the subject is arranged and temporarily affixed to the cranial support. The controller initiates an injury test and commands a motor to oscillate the cranial support to induce rotational accelerations in the subject head. Following a number of oscillations, the injury test is terminated and the subject head and torso detached from the support and stage, and the subject removed from the system.

Figure 1:
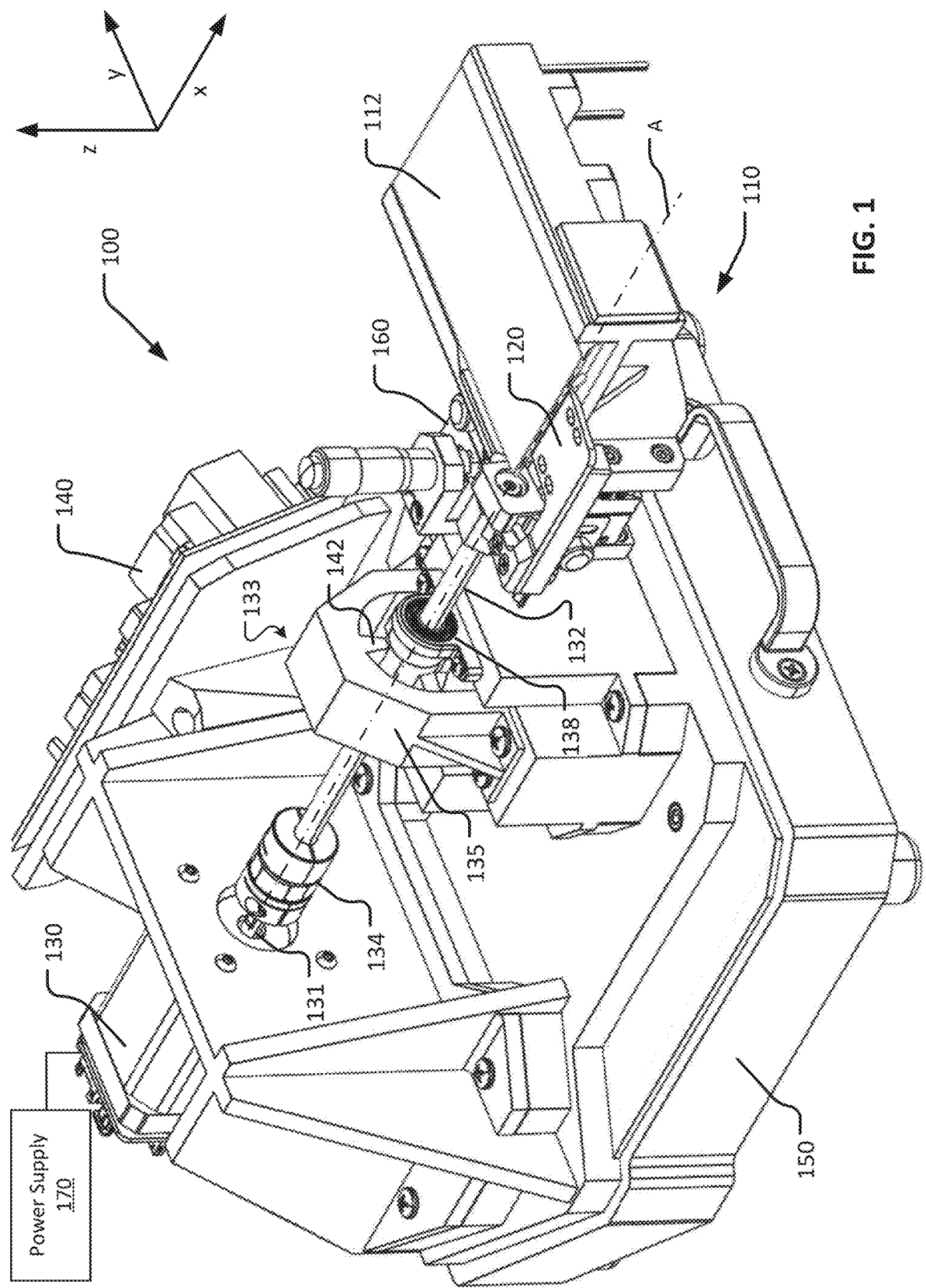
FIG. 1 is a perspective view of an example cranial rotation system.

FIG. 1 depicts a cranial rotation system 100 according to embodiments of the present disclosure. The system 100 is configured to apply an injury test to a subject, which can simulate rotational acceleration-deceleration injury such as abusive head trauma (AHT), shaken-baby syndrome (SBS), or other types of brain damages. The system 100 can be used in pre-clinical research using a rodent as the subject.

In some embodiments, the system 100 includes a support assembly 110, a cranial support 120, a motor 130, and a controller 140. The support assembly 110 is configured to support a subject for injury testing. The cranial support 120 is configured to support a portion of the subject (e.g., head of the subject) and rotate the portion of the subject with respect to the rest of the subject (e.g., the body of the subject) being supported at the support assembly 110. The motor 130 is coupled to the cranial support 120 and configured to rotate the cranial support 120 relative to the support assembly 110. In some embodiments, the cranial support 120 can be attached to the motor 130 via a rotatable shaft 132. The controller 140 is configured to control operation of the motor 130 and/or other components of the system 100 as described herein. In some embodiments, the system 100 includes a base 150 configured to maintain the relative position and orientation of components of the system 100, such as the support assembly 110, the cranial support 120, the motor 130, and the controller 140. The base 150 can provide a stable platform during an injury test.

The system 100 and the components of the system 100 can have dimensions suitable to accommodate and provide a cranial injury test to a small mammalian subject disposed on the support assembly 110, such as young mouse (lissencephalic brain), rat (lissencephalic brain), or ferret (gyrencephalic brain). For example, in some embodiments, the subject is a Sprague-Dawley rat, a Wistar rat, Long-Evans rat, Brown Norway rat, Fischer 344 rat, a house mouse, a deer mouse, white-footed mouse, C57BL/6 mouse, BALB/c mouse, CD-1 mouse, African spiny mouse, B6.129 mouse, Swiss Webster mouse, A/J mouse, transgenic mice and rats (e.g. gene knock-in, conditional gene knock-in, gene knockout, conditional gene knockout, gene modified reporter mice), human disease replicating mice (e.g., APP/PS1 mice), or a Marshall Ferret.

The support assembly 110 can include a subject stage 112 configured to support at least part of the subject (e.g., the body of the subject, the torso). The controller 140 is an electronic device which controls the motor 130 to apply an injury test (e.g., rotation of the head) to the subject placed upon the planar subject stage 112. The controller 140 can receive signals from one or more components of the system 100, such as operating parameters of the motor 130, signals representative of acceleration/deceleration of the cranial support 120, signals representative of angle of the cranial support 120 relative to the subject stage 112, temperature signals at the subject stage 112, etc. The received signals can be used by the controller 140 to adjust the operations of the motor 130 and other components of the system 100 as necessary.

In the illustrated example, the controller 140 is shown to be affixed to the base 150. In various other embodiments, however, the controller 140 can be arranged at different positions. For example, the controller 140 can be a separate device that can be positioned externally to the cranial rotation system 100 and electronically communicates with the system 100 components via a wired or wireless connection. Alternatively, the controller could be secured underneath the base 150.

In some embodiments, the rotatable shaft 132 connects the motor 130 to the cranial support 120. The rotatable shaft 132 is composed of a material that remains rigid and inflexible under the rotational accelerations described. For example, the rotatable shaft 132 can be made of a metal, carbon composite, or plastic polymer. The rotatable shaft 132 can be of solid construction, or hollowed, to adjust the moment of inertia of the rotatable shaft 132. The controller 140 can operate the motor 130 to rotate the rotatable shaft 132 within an angle range. In addition or alternatively, the controller 140 can control the motor 130 to rotate the shaft 132 according to a predetermined acceleration profile, so that the shaft 132 can be rotated at a controlled acceleration. The motor 130 can be of various types. For example, the motor 130 is an electric motor (e.g., a DC motor, an AC motor, stepper motor, brushless motor, brushed motor, or brushed low-inductance pancake motor). The motor 130 can be mounted to the base 150. In some embodiments, the motor 130 includes a drive shaft 131 that can rotate around a rotational axis A.

The drive shaft 131 can be connected to the rotatable shaft 132 so that the rotational axis A of the drive shaft 131 is aligned with a longitudinal axis of the rotatable shaft 132. In some embodiments, the drive shaft 131 is connected to the shaft 132 through a shaft coupling 134, such that rotation of the drive shaft 131 is transferred to rotation of the rotatable shaft 132. When coupled to the rotatable shaft 132, the motor 130 is configured to provide relatively high accelerations to the rotatable shaft 132 and the cranial support 120 connected to the shaft 132. As described herein, the cranial support 120 can further mount one or more sensors, and thus the rotation of the shaft 132 enables the cranial support 120 and the sensors to rotate around the rotational axis A together. The motor 130 can be of various types, such as a stepper motor. An example of the motor 130 is Model No. PD42-3-1241, manufactured by Trinamic Motion Control (Germany). Another example is the series Model No. BE231 Servo Motor, manufactured by Parker. Another example is the Model No. GPN 12-E 005259 Low-Inductance Brushed DC motor, manufactured by Printed Motor Works. The motor can include a high-resolution encoder (e.g., 2,000 or 5,000 lines per revolution).

Figure 2:
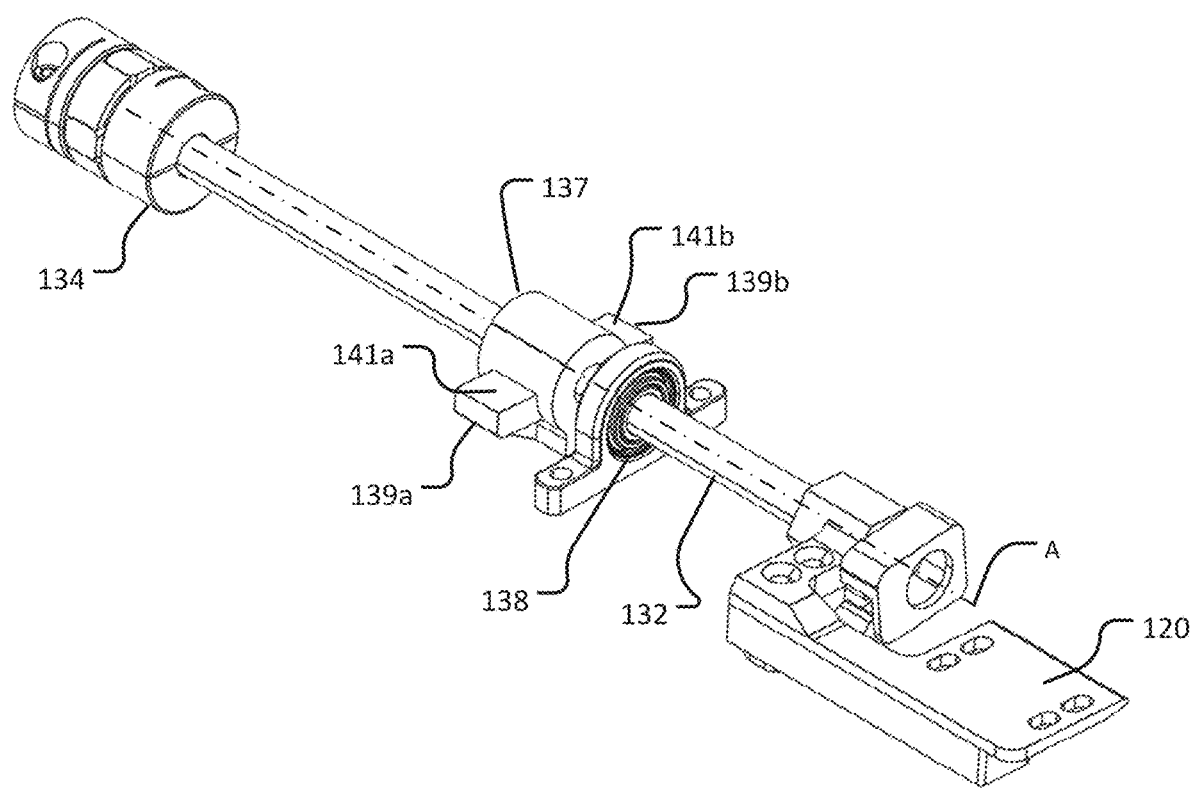
FIG. 2 is a perspective view of an example rotational shaft assembly of the cranial rotation system.

In some implementations the system 100 can include a braking system 133 that controls the operation of the rotatable shaft 132 (and thus the cranial support 12) with further improved accuracy and subject safety. For example, the braking system 133 can be used to prevent a rotation of the shaft 132 beyond a predetermined range, if the motor 130 fails to stop the rotation of its armature as intended to keep the rotation of the shaft 132 within the predetermined range. The braking system 133 is configured to constrain the motion of the rotatable shaft 132. Referring to FIGS. 1 and 2, the braking system 133 can include a brake housing 135, a safety brake 137, and a bearing 138. The brake housing 135 is configured to support the safety brake 137 in place with respect to other components, such as the rotatable shaft 132 and the bearing 138.

The safety brake 137 can be affixed to the rotatable shaft 132 and include one or more stops 139a and 139b (collectively stops 139) configured to restrain the range of rotation of the shaft 132. The stops 139 can be positioned to define an angular range of rotation of the shaft 132. In some embodiments, as illustrated in FIG. 2, two stops 139a and 139b can be positioned at opposing sides of the safety brake 137. Each of the stops 139 includes one or more contact surfaces 141, such as contact surface 141a of the first stop 139a (e.g., the upper surface of first stop 139a) and contact surface 141b of the second stop 139b (e.g., the bottom surface of the second stop 139b). In another embodiment, one or more motional components of the cranial rotation system 100 can include kill-switch, e.g., two or more metal contacts creating a signal when in contact, to prevent movement of the rotatable shaft 132 past the operational range should the motor 130, safety brake 137, or stops 139 not stop the rotational motion during operation.

As the shaft 132 rotates, the safety brake 137 attached to the shaft 132 rotates together, and one or more of the contact surfaces 141 of the stops 139 are configured to contact a portion of the brake housing 135 based on the rotational position of the shaft 132 (and the safety brake 137). As illustrated in FIG. 1, the portion of the brake housing 135 that can engage with the safety brake 137 can include one or more ribs 142 that extend inwardly from an inner circumference of the brake housing 135. The ribs 142 can be positioned at desired locations that allow the ribs 142 to contact the stops 139 of the safety brake 137 at predetermined rotational positions of the shaft 132. The ribs 142 can thereby restrain the angular movement of the shaft 132. The bearing 138 can be affixed to the base 150. The bearing 138 is configured to support the rotatable shaft 132 and permit the rotatable shaft 132 to rotate about the rotational axis A.

In some embodiments, the rotatable shaft 132 is a d-profile shaft having a d-shaped cross section transverse the longitudinal axis. The d-profile facilitates connection between the rotatable shaft 132 and attached components, such as shaft coupling 134, safety brake 137, or cranial support 120, via couplings such as set screws.

Referring again to FIG. 1, the stops 139 of the safety brake 137 rotates as the rotatable shaft 132 rotates. Depending on the angular position of the shaft 132, the stops 139 can contact an arresting feature (e.g., the ribs 142) of the brake housing 135, thereby restricting the rotational motion of the rotatable shaft 132. The arrangement of the stops 139 and the arresting feature of the brake housing 136 can define a maximum angle range between which the rotatable shaft 132 is capable of rotating. Such a maximum angle range can be determined to prevent damage to the cranial support 120, the subject stage 112, other attached components, and/or the subject due to over-rotation of the cranial support 120.

In some embodiments, the cranial rotation system 100 includes a power supply 170 configured to provide electrical power to powered components of the system 100 such as the motor 130, the controller 140, etc. The power supply 170 can be a battery, electric mains, and other suitable electric power sources. In some embodiments, one or more components (e.g., power cords, transformers, etc.) can be provided for connecting the components to the power supply. In some embodiments, the motor 130 and the controller 140 are powered by a single power source. In alternative embodiments, the motor 130 and the controller 140 can be independently powered. In further alternative arrangements, the power is supplied to the controller 140 which supplies power to the motor 130.

Figure 3A:
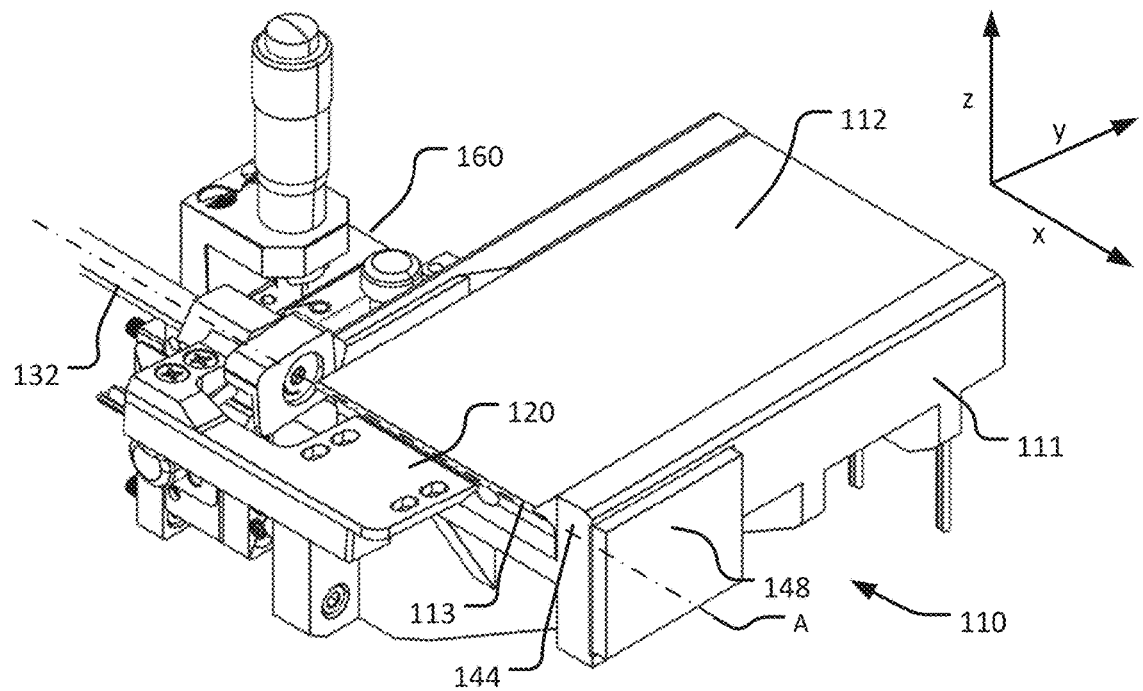
FIG. 3A is a perspective view of an example support assembly in the cranial rotation system.

With reference to FIG. 3A, a closer perspective view of the subject positioning components of the support assembly 110, cranial support 120, and platform positioner 160 are shown. The support assembly 110 includes a platform 111 which holds the subject stage 112. The position of the platform 111 can be controlled by a platform positioner 160 affixed to the base 150 of the cranial rotation system 100. The top of the platform 111 provides a rigid bed configured to position the subject stage 112. The platform 111 can further include sidewalls 144 extending to and coplanar with the top surface of the subject stage 112.

The platform positioner 160 is configured to adjust the position of the support assembly 110 to accommodate subjects of different sizes, and/or for different test purposes. In some embodiments, the platform positioner 160 includes a two-axis linear stage oriented to position the support assembly 110 along the y- and z-axes (shown inset to FIG. 3A). In other embodiments, the platform positioner 160 can adjust the position of the support assembly 110 along different directions, such as x-axis only, y-axis only, z-axis only, x-y axes, x-z axes, or x-y-x axes.

In some embodiments, the platform positioner 160 allows a user to position the platform 111 to within a spatial resolution of, for example, 0.1 millimeters. The platform positioner 160 can be operated manually by the user to adjust the position or the platform 111. Alternatively, the platform positioner 160 can be automatically operated based on a preprogramed algorithm or the user's input.

The platform positioner 160 can move the platform 111 with respect to the base 150 (FIG. 1) to align the longitudinal axis A of the rotatable shaft 132 (e.g., the rotational axis) to be transverse (e.g., perpendicular) to a predetermined portion (e.g., the neck or spine) of the subject for the purpose of the injury test. In some embodiments, the longitudinal axis A is aligned to be transverse to a subject vertebra, particularly a cervical vertebra of the subject spine, such as the C1, C2, C3, C4, C5, C6, or C7 cervical vertebra.

The subject stage 112 rests in the bed of the platform 111 and is positionable along the y-axis. The subject stage 112 provides a planar surface on which to position a prone subject. The subject stage 112 is dimensioned to accommodate the size of the subject. Further, a height of the subject stage 112 is configured to sufficiently define ports 114a and 114b for routing a heating element 116 and a temperature sensor 118 into the subject stage 112. By way of example, a width W (along the x-axis) of the subject stage 112 is 50 mm, a length L (along the y-axis) is 100 mm, and a height H (along the z-axis) is 13 mm. In some embodiments, the width W can be in a range from 25 mm to 100 mm, the length L in a range from 50 mm to 160 mm, and the height H in a range from 5 mm to 25 mm.

In some embodiments, the subject assembly 110 includes a subject restraining mechanism that fixes the subject during the injury test. For example, the subject restraining mechanism includes a strap hole 146, a strap attachment portion 148, and a retraining strap that is routed between the strap hole 146 and the strap attachment portion 148. An example of the restraining strap can include a hook and loop Velcro strap, such as ID TAG HOOK AND LOOP CABLE TIE WITH BUCKLE, McMASTER: 1769N113.

In the illustrated example, the strap hole 146 is defined at one of the sides of the platform 111 and configured to receive the restraining strap therethrough. The strap attachment portion 148 is provided at the other side of the platform 111 and configured to fix one end of the restraining strap. While the one end of the restraining strap remains attached to the strap attachment portion 148, the other end of the restraining strap can be routed through the strap hole 146 and return to the strap attachment portion 148 to be fastened to the one end of the restraining strap at the strap attachment portion 148. The subject can be positioned and restrained under the looped strap above the subject stage 112. Other restraining mechanisms are also possible using other types of fastening devices such as buckles, snaps, tapes, ties, etc.

Figure 3B:
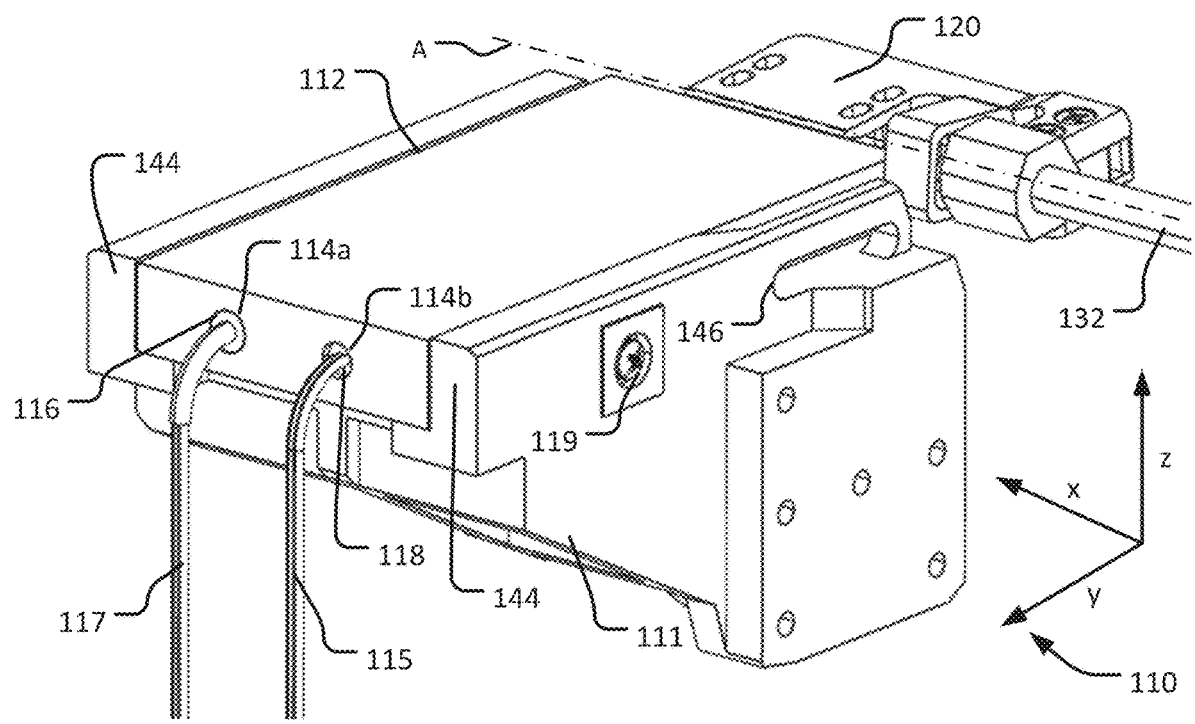
FIG. 3B is another perspective view of the support assembly of FIG. 2A.

Referring to FIG. 3B, another perspective view of the support assembly 110 and platform positioner 160 is shown. Generally, subjects are exposed to an anesthesia treatment before being placed upon the support assembly 110. An anesthetized subject undergoes a reduction in core body temperature which can affect injury test response. To maintain or increase the core body temperature of the subject, the subject stage 112 can be configured to be heated at a predetermined temperature. In some embodiments, the entirety or a portion of the subject stage 112 is composed of a thermally conductive material.

The subject stage 112 can include a heating element 116 configured to heat the thermally conductive portion of the subject stage 112. The heating element 116 can be positioned at various locations. In some embodiments, the subject stage 112 defines a port 114a that extends partially through a length of the subject stage 112 and receives the heating element 116 so that the heating element 116 is circumferentially enclosed in the subject stage 112. Wiring 117 is connected to the heating element 116 and extends out of the subject stage 112. Additionally, the subject stage 112 can include a temperature sensor 118 configured to detect a temperature of the subject stage 112. For example, the subject stage 112 defines a port 114b that extends partially through the length of the subject stage 112 and receives the temperature sensor 118 so that the temperature sensor 118 is circumferentially enclosed in the subject stage 112. Wiring 115 is connected to the temperature sensor 118 and extends out of the subject stage 112. In other embodiments, the temperature sensor 118 can be positioned at different locations suitable for measuring different temperatures, such as a temperature of the subject stage 112, a temperature of the heating element 116 or a temperature of the subject resting on the subject stage 112.

The controller 140 includes a temperature control system which receives temperature signals from the temperature sensor 118 and operates the heating element 116 to raise or lower the temperature of the subject stage 112. In some embodiments, the subject stage 112 can be controlled at a preset temperature value in a range from room temperature, to between 20° C. and 45° C. (e.g., 25° C. and 32° C., or 27° C. and 29° C.). In some embodiments, the subject stage 112 can be controlled around the preset temperature value within a deviation from 0.01° C. to 1° C. (e.g., ±0.01° C., ±0.05° C., ±0.1° C., ±0.5° C., or ±0.9° C.). In this manner the subject targeted temperature can be adjusted to study brain injury under conditions of normothermia, hypothermia, or hyperthermia. The controller 140 can control the subject stage 112 to maintain targeted body temperature and hemodynamics in anesthetized subjects.

In various example embodiments, examples of the thermally conductive materials of the subject stage 112 include metals, ceramics, or thermally conductive polymers. For example, the planar subject stage 112 can be composed of stainless steel, aluminum, alloys thereof, polycrystalline diamond ceramics, aluminum nitride, beryllium oxide, silicon nitride, silicon carbide, ThermaTech™, Makrolon®, or CoolPoly™. In some embodiments, the subject stage 112 is composed of a first material (e.g., a metal) and coated in a second material (e.g., a ceramic).

In some embodiments, the position of the subject stage 112 is adjustable relative to the platform 111. Further, the subject stage 112 can be removable from the platform 111.

For example, the platform 111 includes a stop screw 119 extending through the sidewall 144 and configured to contact a side surface of the subject stage 112. When driven into contact with the side surface of the subject stage 112, the stop screw 119 presses the subject stage 112 against the opposing sidewall 144 of the platform 111 and therefore holds the subject stage 112 in a fixed position relative to the platform 111. Retreating the stop screw 119 out of contact with the subject stage 112 releases the subject stage 112 from the platform 111, so that the subject stage 112 can be adjustable in position or removed from the bed of the platform 111. In some embodiments the bottom surface of the stage 112 and/or the top facing surface of the platform 111 can be modified/treated with materials (e.g., coatings such as Carbinite Metal Coating, polymers, adhesive, or VELCRO) which can increase the friction between both surfaces and enhances the gripping/stability of the stage 112 with the platform 111.

Referring to FIGS. 3C-3E, example configurations of the subject stage 112 are described relative to the cranial support 120. As illustrated in FIG. 3C, the subject stage 112 includes a top surface front edge 113 at an end of the subject stage 112 adjacent to the cranial support 120. In this example, the subject stage 112 has the front edge 113 extending across the entire width W1 of the subject stage 112 (e.g., extending along a transverse axis, e.g., the x-axis). A length L1 of the front edge 113 of the subject stage 112 can be greater than a length L2 of a facing edge 121 of the cranial support 120 that is adjacent to the front edge 113 of the subject stage 112.

Referring to FIG. 3D, in alternative embodiments, the front edge 113 of the subject stage 112 can extend across only a portion of the width W1 of the subject stage 112 such as the shortened front edge 113. In addition, the shortened front edge 113 can be centered on the facing edge 121 of the cranial support 120. For example, the shortened front edge 113 of FIG. 3D recedes along a longitudinal direction of the subject stage 112 and terminates at recessed edges 314a and 314b which extend across the remaining width of the subject stage 112. For example, the recessed edges 314a and 314b can be spaced apart from the shortened front edge 113 by a distance (d) along the longitudinal direction of the subject stage 112. The length L1 of the shortened front edge 113 of the subject stage 112 can be the same as the length L2 of the facing edge 121 of the cranial support 120. Alternatively, the length L1 of the shortened front edge 113 of the subject stage 112 can be smaller or larger than the length L2 of the facing edge 121 of the cranial support 120. The length L1 of the shortened front edge 113, and/or the distance d of the recessed edges 314a and 314b from the shortened front edge 113, can be configured to accommodate the subject limbs during an injury test.

Referring now to FIG. 3E, a side-view of the subject stage 112 is described. The top surface shortened front edge 113 extends along a transverse axis (e.g., the x-axis) across a portion of the width W1 of the subject stage 112, as described above, and extends past a bottom surface front edge 315 (e.g., along the y-axis) of the lower surface of the subject stage 112. In addition, for example, the recessed edge 314a, 314b can have a curved profile between the top and bottom surfaces of the subject stage 112. In another example, the recessed edge 314a, 314b can be linearly sloped between the top and bottom surfaces of the subject stage 112. The recessed edge 314b having a curved, or sloped, profile can position the subject limbs in a beneficial orientation during an injury test. In yet another example, the recessed edge 314a, 314b can be vertical (without curved or sloped profile) between the top and bottom surfaces of the subject stage 112. In some embodiments, the facing edge 121 and the front edge 113 are rounded, sloped, or curved to reduce the likelihood of tearing the neck skin tissue during rapid rotational movements. In some embodiments, a gap of a predetermined distance (e.g., 1 mm or less) is introduced and maintained at the axis of rotation, A, between the facing edge 121 and front edge 113 to further prevent shearing of neck tissue.

Figure 4A:
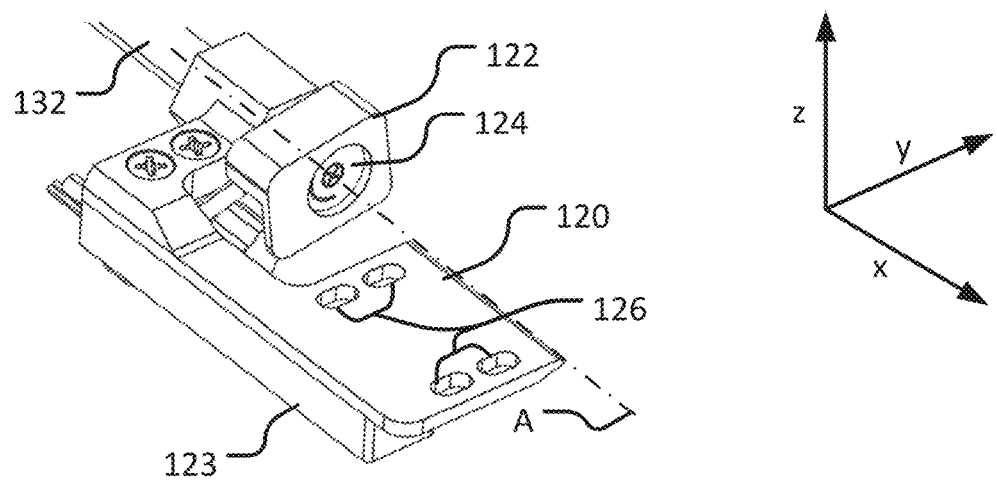
FIG. 4A is a perspective view of an example cranial support in the cranial rotation system.
Figure 4B:
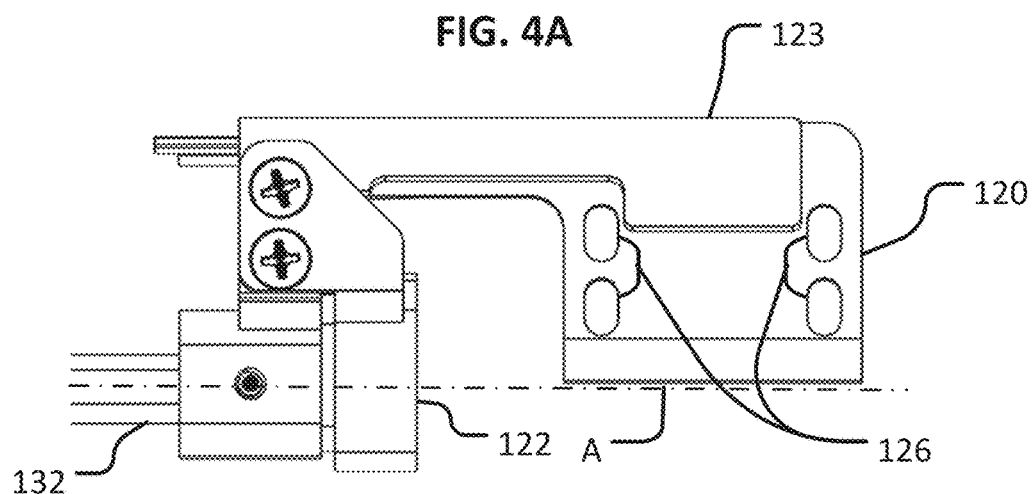
FIG. 4B is a bottom view of the cranial support of FIG. 4A.

Referring to FIGS. 4A and 4B, structural details of the cranial support 120 and attached components are shown. The cranial support 120 is connected to the rotatable shaft 132 and translates a rotational motion along the longitudinal axis of the rotatable shaft 132 (e.g., rotational axis A) to a subject head motion along the subject sagittal plane (e.g., the y-z plane).

The cranial support 120 includes at least one sensor, such as a rotational acceleration sensor, a rotational velocity sensor, a linear acceleration sensor (e.g., accelerometer), a linear velocity sensor, a combined linear-rotational acceleration sensor, a combined linear-rotational velocity sensor, or combinations thereof. For example, the cranial support 120 includes an attached rotational velocity sensor 124 (FIGS. 4A and 4C) and a linear acceleration sensor 125 (shown in FIG. 4C). An example of the rotational velocity sensor 124 is an ARS3 Pro rate sensor manufactured by DTS and an example of a linear acceleration sensor is an ADXL377 sensor manufactured by Analog Devices, Inc. An example of a rotational accelerometer is a piezoelectric Type 8838/8840 sensor manufactured by Kistler, having a dynamic axial range of ±150,000 radians/$s^2$. In the embodiment of FIG. 4A, a first sensor housing 122 and a second sensor housing 123 house the rotational velocity sensor 124 and a linear acceleration sensor 125, respectively. The first sensor housing 122 and second sensor housing 123 are connected to the cranial support 120 such that the housings 122 and 123 move in concert with the cranial support 120 inducing no relative motion during an injury test, such as by screws, clamps, or other temporary means of affixing the components. In some embodiments the motor 130 includes a high resolution encoder, e.g., sensors, that is integrated with or attached to the motor 130 and provides the controller 140 with data on the rotational velocity and acceleration of the motor 130 and/or drive shaft 131.

The cranial support 120 provides a planar support area for the subject head positioned between arresting features 126. The arresting features 126 of FIG. 4A can include holes extending through the cranial support 120 (e.g., holes extending between the upper and lower surfaces of the cranial support 120) through which one or more straps are permanently or temporarily threaded. The straps are connected atop the subject head which constrains head motion to correspond with the cranial support 120 motion. In some embodiments, the arresting features 126 include a clasp, strap, band, buckle, or other permanent or temporary means of affixing the subject head to the cranial support 120.

FIG. 4B shows a view of the cranial support 120 including the arresting features 126 along the z-axis from below. The second sensor housing 123 protects and maintains the position of the linear acceleration sensor 125 (FIG. 4C) with respect to the cranial support 120. The first sensor housing 122 attaches to the cranial support 120 with a pair of screws.

Figure 4C:
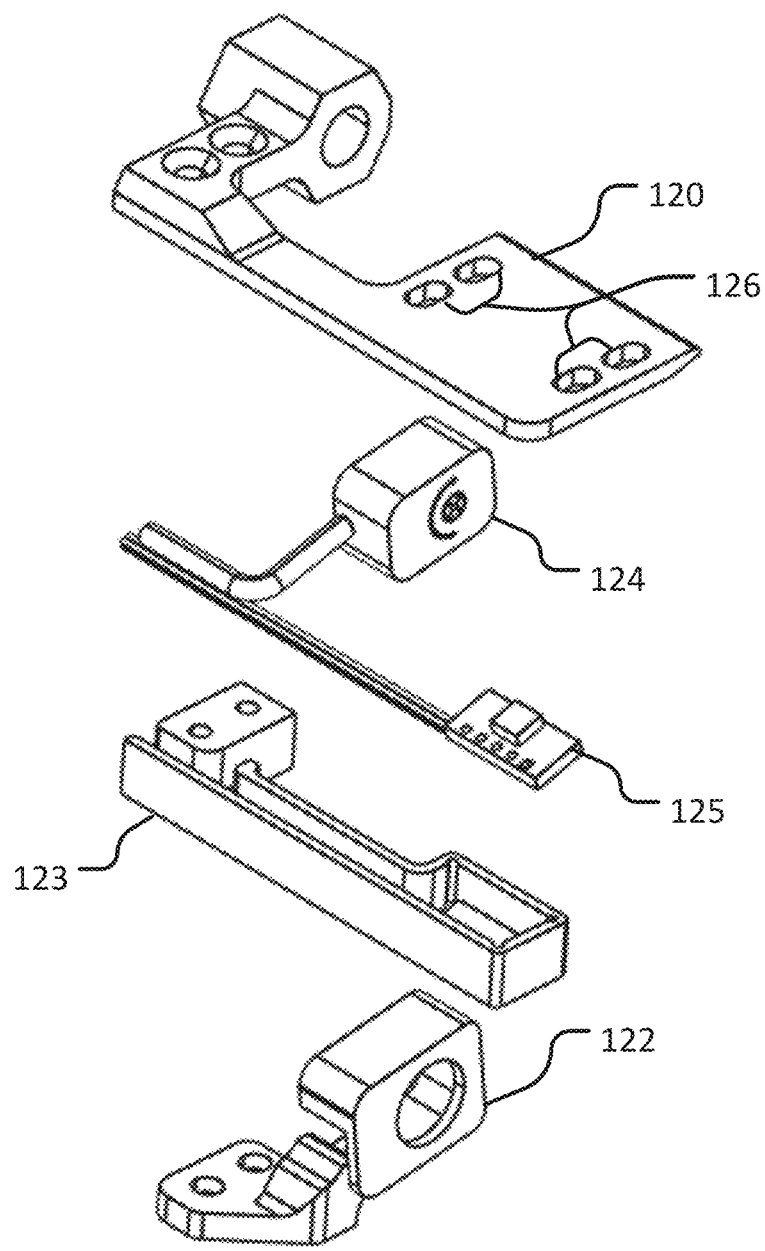
FIG. 4C is an exploded view of the cranial support elements of FIG. 4A.

Referring to FIG. 4C, an exploded view of the cranial support 120, first sensor housing 122, second sensor housing 123, rotational velocity sensor 124, and linear acceleration sensor 125 is shown. The second sensor housing 123 is shaped to receive the linear acceleration sensor 125 and attaches to the cranial support 120. The rotational velocity sensor 124 is housed within the first sensor housing 122 and the center of the rotational velocity sensor 124 is coaxial with the rotational axis A (FIG. 4B). The cranial support 120, first sensor housing 122, and second sensor housing 123 are aligned vertically (e.g., along the z-axis) with the respective assembly as shown in FIG. 4B.

Figure 5A:
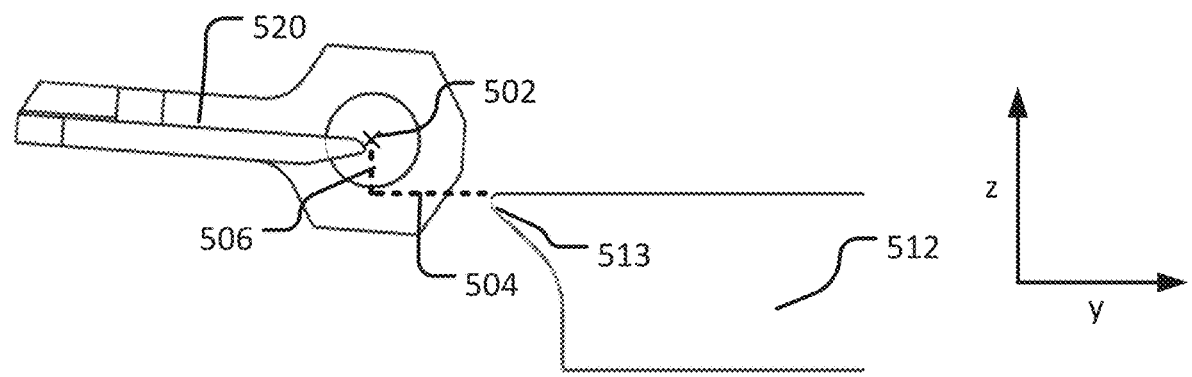
FIG. 5A is a schematic diagram of a relative positioning between the cranial support and the subject stage.
Figure 5B:
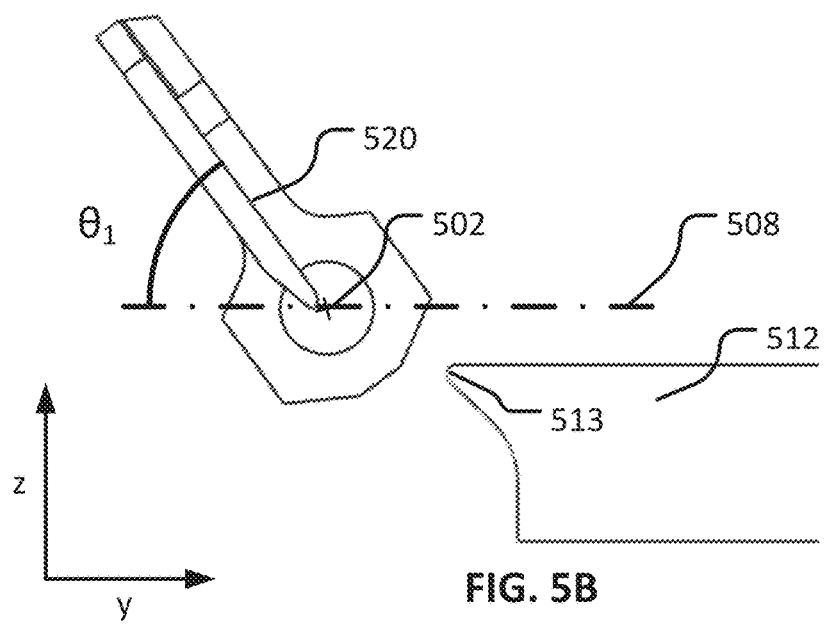
FIGS. 5B and 5C are schematic diagrams of example rotational positioning of the cranial support relative to the subject stage.
Figure 5C:
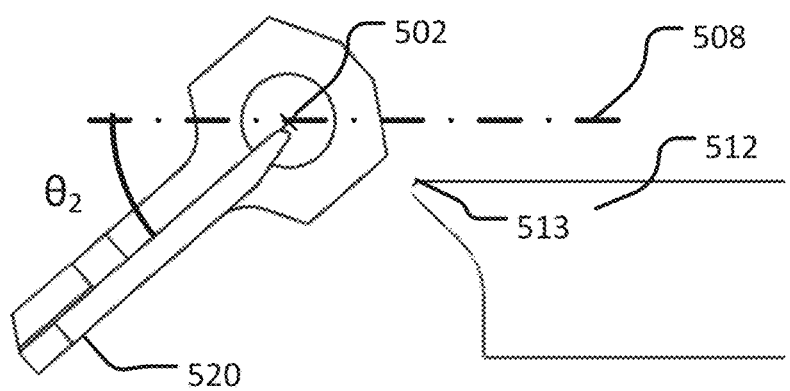

The injury test has increased efficacy and repeatability when the positioning of the subject stage 112 with respect to the cranial support 120 is controlled in a subject-specific manner FIGS. 5A through 5C depict the relative positioning and motions that a cranial support 520 and a subject stage 512 can undergo to position their adjacent edges to support the subject head and torso and align the rotational axis transverse the subject spine. In some embodiments, the cranial support 520 and the subject stage 512 can be implemented by the cranial support 120 and the subject stage 112 described herein.

FIG. 5A depicts a view of the stage 512, a front edge 513 of the stage 512, and the cranial support 520 along the x-axis, parallel with the rotational axis 502 of the cranial support 520 (e.g., along the x-axis of the inset coordinate axes, e.g., the rotational axis A). The y-position of the subject stage 512 is controlled through relative motion of a platform (e.g., relative motion of the platform 111 via the platform positioner 160), through manual or automated positioning of the subject stage 512 in the platform (e.g., in a similar manner that the subject stage 112 is adjustably positioned in the bed of the platform 111), or both. The z-position of the subject stage 512 is controlled through relative motion of the platform (e.g., the relative motion of the platform 111 via platform positioner 160).

Controlling the y- and z-positions orients the front edge 513 of the subject stage 512 with respect to the rotational axis 502. The separation between the rotational axis 502 and the edge 513 includes a y-separation 504 and a z-separation 506. The y-separation 504 and the z-separation 506 can be adjusted to accommodate subjects of different sizes. By way of example, the y-separation 504 can be in a range from 0 mm to 40 mm and the z-separation 506 can be in a range from 0 mm to 40 mm. In other embodiments, the range of the y-separation 504 is between 1 mm and 20 mm, or 5 mm to 10 mm. In other embodiments, the range of the z-separation 506 is between 1 mm and 10 mm, or 3 mm to 7 mm. Higher values for the y-separation 504 and z-separation 506 accommodate larger subjects (e.g., neonatal ferrets) while lower values accommodate smaller subjects (e.g., neonatal mice).

Referring to FIGS. 5B and 5C, a rotational range of motion of the cranial support 520 with respect to a plane 508 parallel with the top surface of the subject stage 512 (e.g., dotted line in FIGS. 5A and 5C, e.g., the x-y plane) is depicted. The cranial support 520 rotates around the rotational axis 502 between a first angle, $\theta_1$, and a second angle, $\theta_2$, as shown in FIGS. 5B and 5C, respectively. FIG. 5B shows the cranial support 520 rotated to $\theta_1$ above the plane 508 and FIG. 5C shows the cranial support 520 rotated to $\theta_2$ below the top surface of the subject stage 512.

The first and second angles $\theta_1$ and $\theta_2$ can have equal values, or different values. The first angle $\theta_1$ can be greater than the second angle $\theta_2$, or less than the second angle $\theta_2$. The maximum values of the first and second angles $\theta_1$ and $\theta_2$ (e.g., $\theta_{1,MAX}$ and $\theta_{2,MAX}$) are delimited by, for example, the stops 139, and the rib 142 of the brake housing 135 while the motor 130 controls the rotation as described herein. In other embodiments, the motor 130 can control the rotation within an angle range $\Delta\theta$ (e.g., $\Delta\theta=\theta_1+\theta_2$) that is less than the maximum $\Delta\theta_{MAX}$ (e.g., $\Delta\theta_{MAX}=\theta_{1,MAX}+\theta_{2,MAX}$). The injury thresholds that produce neuropathology (e.g., bleeding/hemorrhage, tissue death) may be different on each side of the brain. Independent control of both the angle $\theta$ and peak acceleration of the swing in the flexion (e.g., downward with respect to plane 508) and extension (e.g., upward with respect to plane 508) directions can facilitate (and allow the user to program) a range of insult severities that can create unique patterns of tissue damage to study regional vulnerability, which may shed light on injury thresholds at different loci in the subject brain.

Figure 5D:
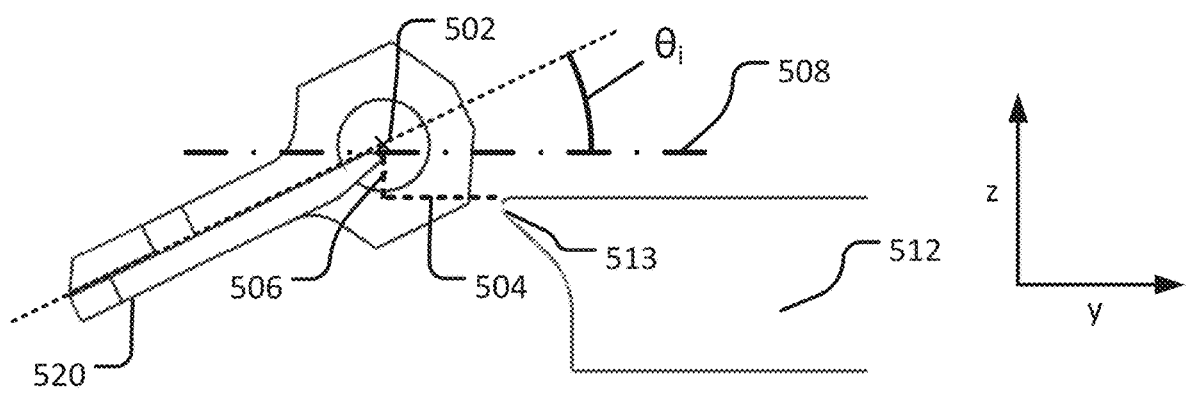
FIG. 5D is a schematic diagram of a relative positioning between the cranial support and the subject stage in which the cranial support has a first initial angle with respect to the subject stage.

In some embodiments, and with reference to FIG. 5D, the cranial support 520 can be oriented at a third angle $\theta_i$ with respect to the plane 508 (e.g., an initial angle) and the cranial support 520 can be rotated around the rotational axis 502 through the angle range $\Delta\theta$ around third angle $\theta_i$.

During an injury test, where the configurations of FIGS. 5A-C are used with the components of FIGS. 1-4, the motor 130 rotates the rotatable shaft 132, and thereby rotates the cranial support 520 between the first and second angles $\theta_1$ and $\theta_2$ via the rotatable shaft 132 at a frequency. In some embodiments, the frequency is in a range from 0 Hz to 10 Hz. In other embodiments, the frequency ranges from 1 Hz to 6 Hz. In yet other embodiments, the frequency is in a range from 2 Hz to 4 Hz. In various example embodiments, $\Delta\theta$ is in a range from 1° to 160° (e.g., $1°\leq\Delta\theta\leq160°$). For example, $\Delta\theta$ can be 90° (e.g., $\theta_1$ and $\theta_2=45°$). An injury test can include a number of complete oscillations in which the cranial support 520 is controlled to $\theta_1$, to $\theta_2$, and again to $\theta_1$. The number of complete oscillations can be in a range from 0.5 oscillation to 200 oscillations. Each oscillation can include two individual swings, one being in one direction and the other being in the returning direction. In other embodiments, the number of complete oscillations can be in a range from 10 oscillation to 150 oscillations. In yet other embodiments, the number of complete oscillations can be in a range from 50 oscillation to 100 oscillations.

The acceleration applied to the subject head is a controlled parameter in the injury test, with higher accelerations inducing more subject injury. The motor 130 rotates the cranial support 520 through a complete oscillation, e.g., between $\theta_1$ and $\theta_2$, such that the rotational acceleration of the cranial support 520 is in a range, for example, from 500 radians/s$^2$ and 75,000 radians/s$^2$. In other embodiments, the rotational acceleration in a range from 30,000 radians/s$^2$ and 50,000 radians/s² or in yet other embodiments, the rotational acceleration in a range from 20,000 radians/s² and 30,000 radians/s². Subjects having a smaller mass have a smaller proportional brain mass which has the smaller inertia. In such cases, greater radial acceleration is needed to generate shearing forces that produce an injury in the subject.

Figure 6:
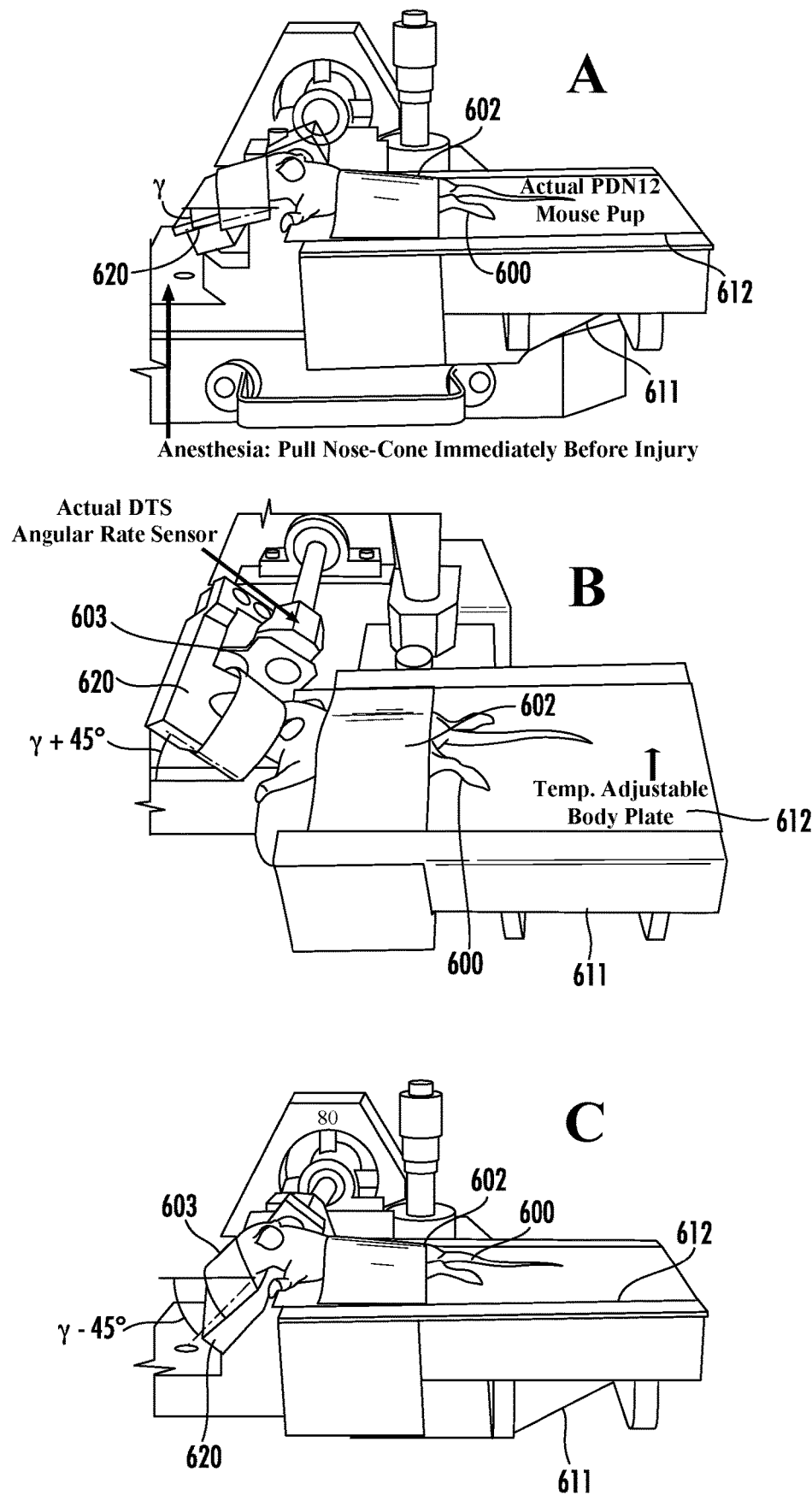
FIG. 6 illustrates an example operation of the cranial rotation system with a rodent subject.

FIG. 6 is a series of three images depicting the positioning of a subject 600 (e.g., a murine subject, e.g., a PND12 mouse pup) on a stage 612 arranged in a platform 611. The head of the subject 600 is affixed to a cranial support 620. The stage 612, the platform 611, and the cranial support 620 can be implemented by the stage 512, 112, the platform 111, and the cranial support 520, 120, respectively.

The images are example images of the positioning and orientation during an injury test in which the head of the subject 600 is rotated through a 90° angle. The body of the subject 600 is temporarily affixed to the stage 612 with a first piece of tape 602 and the head of the subject 600 is temporarily affixed to the cranial support 620 with a second piece of tape 603.

The upper most image of FIG. 6 (e.g., the image with "A" inset in the upper right corner) depicts the subject 600 in a first position with the cranial support 620 at an initial angle γ (e.g., dashed line) with respect to a plane parallel (e.g., solid line) with the top surface of the stage 612. The starting angle is determined in part by the choice of producing the first insult either to the top of the brain (dorsal injury) or to the bottom of the brain (ventral injury), e.g., low starting angles facilitate dorsal injuries during the first insult and high angles facilitate ventral injuries. The middle image of FIG. 6 (e.g., the image with "B" inset in the upper right corner) depicts the cranial support 620 rotated upward by 45° with respect to the initial angle γ (e.g., γ+45°). The bottom image of FIG. 6 (e.g., the image with "C" inset in the upper right corner) depicts the cranial support 620 rotated downward by 45° with respect to the rest angle γ (e.g., γ−45°).

Figure 7:
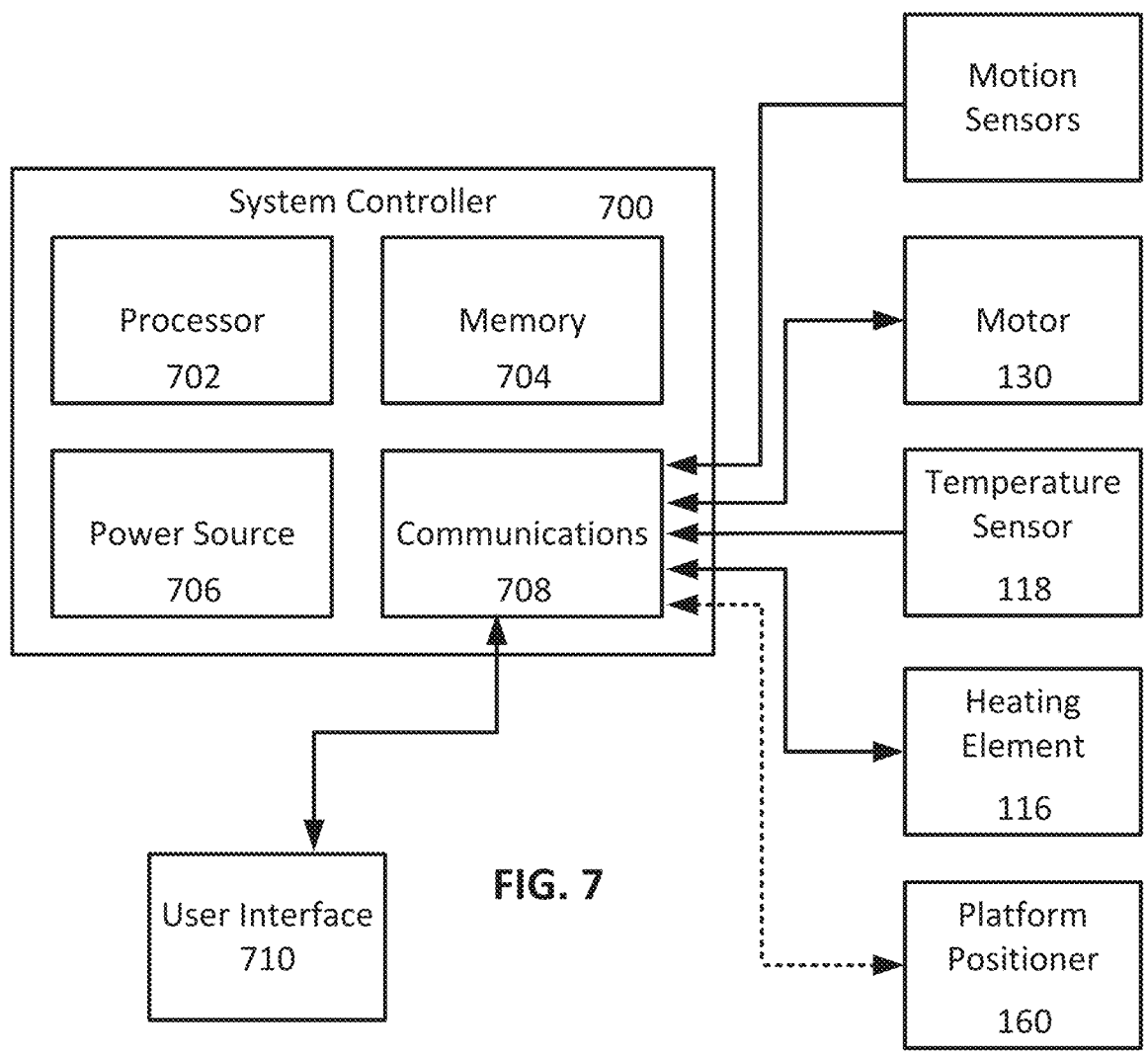
FIG. 7 is a block diagram of an example controller of the cranial rotation system that communicates with components of the cranial rotation system.

FIG. 7 is a block diagram of an example controller 700, such as controller 140. The controller 700 includes a processor 702, computer memory 704, power supply 706 (e.g., or connection to a power source, described above), and a communications array 708. The controller 700 utilizes the processor 702, memory 704, and communications array 708 to receive data from and provide commands to attached components, such as the motor 130, heating element 116, and temperature sensor 118, depicted by the two-way arrows of FIG. 7. In some embodiments, the controller 700 can receive input from and control the platform positioner 160 to control the relative position between the cranial support 120 and the support assembly 110.

The processor 702 is generally a device for receiving input, performing logical operations on data, and providing output. The processor 702 can be a central processing unit, a microprocessor, general purpose logic circuity, application-specific integrated circuity, a combination of these, and/or other hardware for performing the functionality needed.

The memory 704 is generally one or more devices for storing data. The memory 704 can include long term stable data storage (e.g., on a hard disk), short term unstable (e.g., on Random Access Memory) or any other technologically appropriate configuration. In some embodiments, the controller 700 stores data received from the attached components (e.g., motor 130, heating element 116, and/or temperature sensor 118) within memory 704 for later processing or presentation.

In general, the power supply 706 includes hardware used to receive electrical power from a source and supply it to components of the controller 700. The power supply can include, for example, a battery pack. In some embodiments, the power supply can further include ports to receive electrical power from a wall outlet adapter, an AC to DC converter, a DC to AC converter, a power conditioner, a capacitor bank, and/or one or more interfaces for providing power in the current type, voltage, etc., needed by other components of the controller 700.

A communications array 708 allows the controller 700 to communicate with other components of the system 100. In some embodiments, the controller 140 includes components for wired or wireless communication with external components and provides any technologically appropriate communication interface, including but not limited to multiple communication interfaces such as USB, Lightning®, cellular, Wi-Fi, Bluetooth®, and copper wired networks. In some embodiments, the controller 700 can be, or communicate with a software application stored on the memory (e.g., an installed application, an app) of a mobile device, or networked device.

The communications array 708 provides electronic communication between the attached components and controller 700, of which controller 140 is an example. The communications array 708 receives data from motor 130, heating element 116, and/or temperature sensor 118, (and optionally platform positioner 160) and includes additional integrated components, such as microcontrollers, transceivers, amplifiers, filters, and/or A/D converters, to process received data into signals which the communications array 708 supplies to the controller 700. In some embodiments, the communications array 708 includes interfaces for a portable memory and/or storage device (e.g., USB drive). The portable device can be connected to the communications array 708 and one or more treatment parameters can be received by the controller 700.

In some embodiments, the controller 700 can include a user interface 710 which facilitates interaction with a user. For example, in some embodiments, the user interface 710 can include a display for displaying information (e.g., data) to the user, and/or receiving input from the user. The user interface 710 can be a computing device (e.g., a laptop, tablet, personal computer, smart phone, networked computing device) having a screen (e.g., a touchscreen) and/or one or more input device (e.g., keyboard, button, dial). The user interface 710 can communicate with the communications array 708 using a wireless or wired interface.

The controller 700 includes in memory 704 a data structure (e.g., an injury test file) including one or more injury test values corresponding to an injury test to be applied to the subject. The data structure can include one or more injury test parameters, including a temperature value, temperature profile, acceleration value, velocity value, acceleration profile, velocity profile, angle value, angle profile, frequency value, time period, and/or oscillation value. A profile is a consecutive series of values across a time period and, in some embodiments, can constitute a signal function profile, such as a sinusoidal profile, a saw tooth profile, or a triangle profile.

In some embodiments, the injury test file can include subject-related injury test parameters such as subject species, subject dimensions (e.g., length, width, or height), subject mass, subject sex, or subject temperature. In some embodiments, the injury test parameters can be input or modified into the controller 700 through the user interface 710, stored and accessed locally in memory 704, or received from a networked location via communications array 708.

The controller 700 controls the attached components to achieve the values and profiles stored in memory 704. In one example, a temperature profile includes a consecutive series of temperature values across an injury test time period. The controller 700 receives temperature signals from the temperature sensor 118, compares the temperature signal to the temperature profile stored within the injury test file, and controls the heating element 116 to modify (e.g., raise or lower) the temperature of the subject stage 112 until the temperature signal received from the temperature sensor 118 is within a temperature range (e.g., resolution of the temperature sensor 118) of the temperature profile. The controller 700 can modify the stage 112 temperature according to the temperature profile before, during, or after the injury test. In some embodiments, the temperature profile corresponds to a subject temperature, e.g., a subject basal temperature.

The controller 700 receives a motion signal from each of the connected motion sensors. In some embodiments, the motion signals are accelerations signals from acceleration sensors. In addition or alternatively, the motion signals can include velocity signals, position signals, or a combination of acceleration, velocity, and position signals. In embodiments in which the cranial rotation system 100 includes more than one motion sensors providing a signal to the controller 700, the controller 700 includes an algorithm for determining a motion value, such as a rotational acceleration value, from the received signals. The controller 700 can perform similar operations (e.g., receive a signal and provide commands) to control the motor 130 to achieve one or more motional profiles, such as the acceleration profile, velocity profile, or angle profile. In some embodiments, the controller 700 can control the platform positioner 160 based upon at least a platform position value.

For example, as described herein, the cranial rotation system 100 can include the rotational velocity sensor 124 in the first sensor housing 122 and the linear acceleration sensor 125 in the second sensor housing 123. The rotational velocity sensor 124 provides a rotational velocity signal to the controller 700 corresponding with the rotational velocity (ω) of the sensor 124. The linear acceleration sensor 125 provides a signal to the controller 700 corresponding with the linear acceleration (α) of the sensor 125. The signal of the rotational velocity sensor 124 corresponds with the rotational velocity of the cranial support 120 about the rotational axis 502, and the linear acceleration sensor 125 corresponds with the linear acceleration of the cranial support 120, due to the first sensor housing 122 and second sensor housing 123 being affixed to the cranial support 120 and measuring the respective velocity and acceleration in the rotating reference frame of the rotational axis 502.

Without wishing to be bound by theory and by way of example, the controller 700 commands the processor 702 to calculate an angular acceleration (α) around the rotational axis 502 according to the equations: $\alpha_\omega = d\omega/dt$ and $\alpha_l = \alpha/r$ where r is the radial distance between the linear acceleration sensor 125 and the rotational axis 502. The radial distance, r, can be a value stored in memory 704. The rotational velocity sensor 124 and linear acceleration sensor 125 provide the $\alpha_\omega$ and $\alpha_l$ to the controller 700 as motion signals.

To determine that the signals received from the linear acceleration sensor 125 and the rotational velocity sensor 124 correlate with one another, the controller 700 includes in memory 704 an algorithm to calculate a correlation coefficient. For example, the algorithm can calculate a Pearson correlation coefficient. The Pearson correlation coefficient is a measure of linear correlation between two sets of data. It is the covariance of two variables, divided by the product of their standard deviations, e.g., a normalized measurement of the covariance, such that the result always has a value between −1 and 1.

Without wishing to be bound by theory and by way of example, the Pearson correlation coefficient can be calculated by the controller 700 with the received $\alpha_\omega$ and $\alpha_l$ using the equation:

$$r = \frac{\sum_k (a_{\omega,i} - \overline{a_\omega})(\alpha_{l,i} - \overline{\alpha_l})}{\sqrt{\sum_k (a_{\omega,i} - \overline{a_\omega})^2} \sqrt{\sum_k (a_{l,i} - \overline{a_l})^2}}$$

If the calculated Pearson correlation coefficient is beneath a correlation coefficient threshold stored in memory 704, the controller 700 can display an error message indicating that the sensors are not within the threshold range. For example, the correlation coefficient threshold can be 0.95, 0.90, or 0.99.

Figure 8:
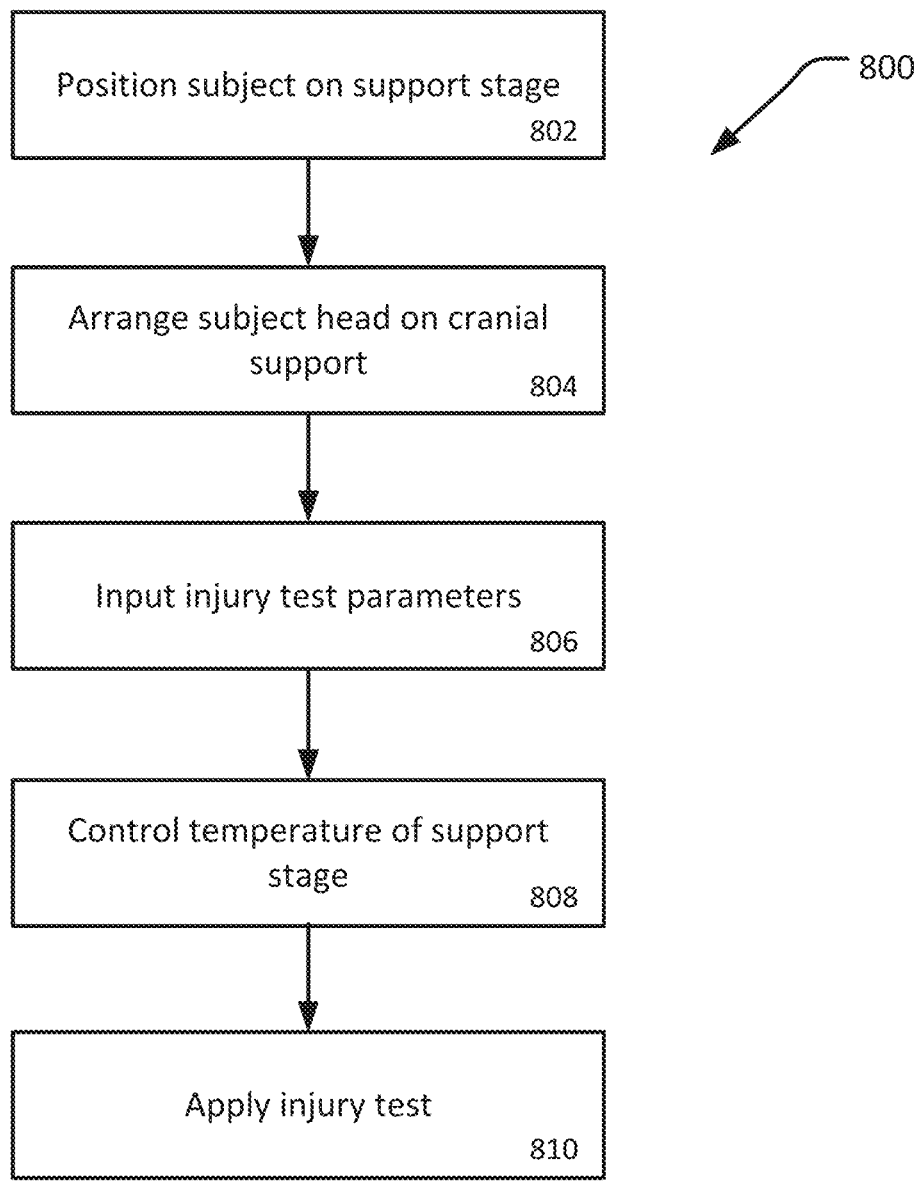
FIG. 8 is a flow chart illustrating an example method for performing a head injury test.

FIG. 8 is a flow chart diagram describing an example process of an injury test for which the cranial rotation system 100 can be used. The subject is placed prone onto the subject stage 112 of the support assembly 110 (step 802). The torso of the prone subject is arranged such that the abdominal wall is in contact with the subject stage 112. In general, the subject can be a living subject or an expired subject. Living subjects can be anaesthetized to prevent subject motion during the injury test. In embodiments in which the support assembly 110 includes temporary restraints, the subject is restrained to the subject stage 112.

The subject head is arranged onto and temporarily arrested against the cranial support 120 (step 804). The head is arranged such that the floor of the lower jaw (e.g., the chin) is in contact with the planar surface of the cranial support 120. The head is temporarily restrained to the cranial support 120 through the use of one or more temporary restraints, described above.

The controller 140 receives injury test parameters (step 806). The controller 140 can receive injury test parameters from a data structure (e.g., injury test file) stored in memory 704, from a remote location accessible by network (e.g., the internet), from an application on a mobile device, or from a user input device connected to the controller 140. In some embodiments, the controller 140 can receives injury test parameters from the data structure, and present a prompt to a user to verify/modify one or more parameters/values within the data structure.

The controller 140 receives a temperature signal from the temperature sensor 118 and operates the heating element 116 to achieve a temperature value stored in the injury test file (step 808). The controller 140 compares the temperature signal to a temperature value and/or a temperature profile and operates the heating element 116 to raise or lower the temperature of the subject stage 112 to within a resolution range of the temperature value.

The controller 140 commands the motor 130 to operate according to one or more parameters of the injury test file (step 810). For example, the controller 140 commands the motor 130 to operate according to an acceleration value, and/or an acceleration profile. The motor 130 provides torque to the rotatable shaft 132 connected to the cranial support 120, which causes the cranial support 120 to rotate in the y-z plane (e.g., the sagittal plane of the subject).

The controller 140 commands the motor 130 to cause motion in the cranial support 120 for a time period and/or a cycle count. The motor 130 ceases once the time period and/or the cycle count is elapsed. The temporary restraints are detached from the subject, and the subject removed from the cranial rotation system 100.

While this specification contains many specific implementation details, these should not be construed as limitations on the scope of any inventions or of what may be claimed, but rather as descriptions of features specific to particular embodiments of particular inventions. Certain features that are described in this specification in the context of separate embodiments can also be implemented in combination in a single implementation. Conversely, various features that are described in the context of a single implementation can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the subject matter have been described. Other embodiments are within the scope of the following claims. In some cases, the actions recited in the claims can be performed in a different order and still achieve desirable results. In addition, the processes depicted in the accompanying figures do not necessarily require the particular order shown, or sequential order, to achieve desirable results. In certain embodiments, multitasking and parallel processing may be advantageous.

What is claimed is:

1. A cranial rotation system for optimized injury observation, the cranial rotation system comprising:
   a subject stage configured to support at least one part of a subject;
   a cranial support configured to support a cranium of the subject and rotate relative to the subject stage;
   a motor configured to rotate the cranial support about a rotational axis, whereby the cranial support is oscillated, thereby inducing injury to at least one part of the cranium of the subject; and
   a controller, the controller being configured to operate the motor, wherein the motor is configured to repeat a frequency of oscillation of the cranial support for a predetermined period of time.

2. The cranial rotation system of claim 1, wherein the cranial support is disposed at an end of the subject stage.

3. The cranial rotation system of claim 1, wherein the subject stage includes a heating element in electrical connection with the controller, the controller configured to control a temperature of the heating element.

4. The cranial rotation system of claim 3, wherein the subject stage includes a temperature sensor configured to detect a temperature at the subject stage and transmit a temperature signal to the controller, the temperature signal being representative of the detected temperature, and wherein the controller is configured to operate the temperature of the heating element based at least in part upon the temperature signal.

5. The cranial rotation system of claim 1, wherein the cranial support includes an acceleration sensor configured to detect an acceleration of the cranial support and transmit an acceleration signal to the controller, the acceleration signal being representative of the detected acceleration, and wherein the acceleration sensor is a rotational acceleration sensor, a linear acceleration sensor, or both.

6. The cranial rotation system of claim 5, wherein the cranial support includes a velocity sensor configured to detect a velocity of the cranial support and transmit a velocity signal to the controller, the velocity signal being representative of the detected velocity, and wherein the velocity sensor includes a rotational velocity sensor, a linear velocity sensor, or both.

7. The cranial rotation system of claim 6, wherein the controller is configured to operate the motor based at least in part upon the velocity signal or an acceleration signal.

8. The cranial rotation system of claim 1, wherein the subject stage has a first end and a second end opposite to the first end, the first end being closer to the cranial support than the second end, and the first end extending along a transverse axis across a width of the subject stage, and wherein the rotational axis of the cranial support is arranged parallel with the transverse axis and is elevated above a top surface of the subject stage.

9. The cranial rotation system of claim 1, further comprising:
   a platform configured to receive the subject stage; and
   a platform positioner configured to alter a position of the platform.

10. The cranial rotation system of claim 9, wherein the platform positioner includes a position sensor and is configured to detect a position of the platform positioner and transmit a position signal to the controller, the position signal being representative of the position of the platform positioner along at least one spatial dimension, wherein the controller is configured to receive a position value from the platform positioner and control the platform positioner based on at least the position value.

11. The cranial rotation system of claim 1, wherein the cranial support includes a motion sensor configured to detect a motion of the cranial support and transmit a motion signal to the controller, the motion signal being representative of the detected motion, wherein the motion sensor is at least one of a linear velocity sensor, a rotational velocity sensor, a linear acceleration sensor, or a rotational acceleration sensor, and wherein the controller is configured to operate the motor based at least in part upon the motion signal.

12. The cranial rotation system of claim 1, wherein the cranial support includes two or more motion sensors and the controller is configured to receive two or more motion signals from the two or more motion sensors and calculate a correlation coefficient between the two motion signals, wherein the two or more motion sensors are selected from a group consisting of a linear velocity sensor, a rotational velocity sensor, a linear acceleration sensor, and a rotational acceleration sensor, and wherein the controller is configured to operate the motor based at least in part upon the two or more motion signals.

13. The cranial rotation system of claim 1, further comprising a braking system, wherein the braking system is configured to constrain a rotation of the cranial support beyond a predetermined range, thereby preventing injury to at least one part of the cranium of the subject greater than induced by the motor during the repeated frequency of oscillation of the cranial support for the predetermined period of time.

14. A method for optimizing injury observation of a subject using a cranial rotation device, the method comprising:
providing a cranial rotation device, the cranial rotation device comprising:
a subject stage configured to support at least one part of a subject;
a cranial support configured to support a cranium of the subject, rotate relative to the subject stage;
a motor configured to rotate the cranial support about a rotational axis; and
a controller, the controller being configured to operate the motor;
positioning the at least one part of the subject on the subject stage;
arranging a cranium of the subject on the cranial support; and
activating the motor, via the controller, to rotate the subject stage in an angle range around an axis at a frequency for a predetermined period of time, whereby the cranial support is oscillated, thereby inducing injury to at least one part of the cranium of the subject.

15. The head rotation method of claim 14, wherein the rotation of the subject stage is in a flexion direction and/or an extension direction based on the orientation of the subject head.

16. The head rotation method of claim 14, wherein the axis is perpendicular to a spine of the subject, wherein the axis intersects the spine of a subject at a cervical vertebrae.

17. The head rotation method of claim 14, wherein the angle range is within ±80° of a top surface plane of the subject stage.

18. The head rotation method of claim 14, wherein the device includes a heating element and a temperature sensor, and the method includes determining a temperature value of the subject stage and controlling the heating element based on the temperature value.

19. The head rotation method of claim 14, including measuring an acceleration value of the cranial support and controlling the motor based upon the acceleration value.

20. The head rotation method of claim 19, wherein the method includes calculating a correlation coefficient based upon at least one the acceleration signal, directly measured via at least one sensor, by a mathematical derivation of acceleration from rotational velocity data, or any combination thereof.

* * * * *